United States Patent [19]

Naylor et al.

[11] Patent Number: 5,116,842
[45] Date of Patent: * May 26, 1992

[54] CHEMICAL COMPOUNDS

[75] Inventors: Alan Naylor, Royston; Duncan B. Judd, Stanstead Abbots, both of England

[73] Assignee: Glaxo Group Limited, London, England

[*] Notice: The portion of the term of this patent subsequent to Jul. 24, 2007 has been disclaimed.

[21] Appl. No.: 524,441

[22] Filed: May 17, 1990

[30] Foreign Application Priority Data

May 18, 1989 [GB] United Kingdom ............... 8911451
May 18, 1989 [GB] United Kingdom ............... 8911452

[51] Int. Cl.$^5$ ................... A61K 31/495; C07D 403/06
[52] U.S. Cl. ..................................... 514/252; 549/372
[58] Field of Search ................. 544/372; 514/252

[56] References Cited

U.S. PATENT DOCUMENTS

| | | | |
|---|---|---|---|
| 3,184,463 | 5/1965 | Irikura et al. | 544/387 |
| 3,324,128 | 6/1967 | Irikura et al. | 544/387 |
| 3,347,860 | 10/1967 | Irikura et al. | 544/387 |
| 4,705,781 | 11/1987 | Boast | 544/337 |
| 4,923,863 | 5/1990 | Scopes et al. | 544/141 |
| 4,943,578 | 7/1990 | Naylor et al. | 544/367 |

FOREIGN PATENT DOCUMENTS

| | | |
|---|---|---|
| 86/66824 | 6/1987 | Australia . |
| 256890 | 2/1988 | European Pat. Off. . |
| 260041 | 3/1988 | European Pat. Off. . |
| 275696 | 7/1988 | European Pat. Off. . |
| 330461 | 8/1989 | European Pat. Off. . |
| 330467 | 8/1989 | European Pat. Off. . |
| 346115 | 12/1989 | European Pat. Off. . |
| 368670 | 5/1990 | European Pat. Off. . |
| 88/01131 | 2/1988 | World Int. Prop. O. . |

OTHER PUBLICATIONS

Br. J. Pharmacol., 1989, 96, 986–992.
Naylor et al., Chem. Abst. 112-198421k (1990).
Terada et al., Chem. Abst 113-78419q (1990).

*Primary Examiner*—Cecilia Shen
*Attorney, Agent, or Firm*—Bacon & Thomas

[57] ABSTRACT

Compounds are disclosed of formula (I)

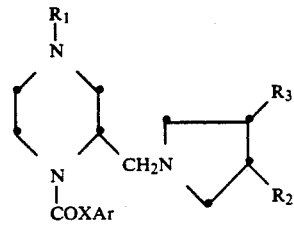

wherein $R_1$ represents —$COR_4$, —$CO_2R_4$, —$COCO_2R_4$ or —$CONR_4R_5$ (where $R_4$ and $R_5$ may be the same or different and represent a hydrogen atom or a $C_{1-3}$ alkyl group);

$R_2$ represents a hydrogen atom or a hydroxy or oxo group, with the proviso that when $R_1$ is —$COR_4$, —$CO_2R_4$ or —$COCO_2R_4$, $R_2$ is not a hydrogen atom;

$R_3$ represents a hydrogen atom or a hydroxy group;
X represents a direct bond, —$CH_2$— or —$CH_2O$—;
Ar represents a substituted phenyl moiety; and physiologically acceptable salts thereof.

The compounds are indicated as useful in the treatment of pain.

Processes for their preparation and pharmaceutical compositions containing them are also disclosed.

20 Claims, No Drawings

CHEMICAL COMPOUNDS

This invention relates to piperazine derivatives, to processes for their preparation, to pharmaceutical compositions containing them and to their medical use. In particular, the invention relates to compounds which act as agonists at kappa opioid receptors.

Compounds which are kappa opioid receptor agonists have been indicated in the art for the treatment of a number of conditions and have been described, for example, as analgesics, as diuretics and in the treatment of cerebral ischaemia.

Kappa opioid receptor agonists have been shown to reduce plasma vasopressin levels by inhibiting vasopressin release from the terminals of the magnocellular neurones in the posterior pitutary (see Bicknell R. J., Chapman C., and Zhao B-G, J. Physiol., 388, 98 (1987)). Inhibition of vasopressin release is considered beneficial in the treatment of congestive heart failure and hypertension.

Kappa opioid receptors have also been shown to be present on the peripheral terminals of primary afferent fibres where they cause inhibition of neurogenically mediated plasma extravasation (see Russell N. J. W. Jamieson A., Callen T. S. and Rance M. J., Br. J. Pharmacol., 86, 788P (1985)). Kappa receptor agonists are therefore indicated in the treatment of conditions where the pathology involves the release of mediators from the peripheral terminals of sensory afferents such as pain, asthma, itch, psoriasis and inflammatory disorders.

A number of classes of compounds which act as agonists at kappa opioid receptors have been disclosed in the art.

Piperidine derivatives having kappa receptor agonist activity of use in the treatment of pain are disclosed, for example, in published Australian Patent Application No. 86/66824 and published European Patent Application Nos. 260041 and 275696. Piperidine derivatives having kappa receptor agonist activity of use in the treatment of pain and cerebral ischaemia are described in published European Patent Application No. 330461.

Morpholine derivatives having kappa agonist activity of use in the treatment of pain and cerebral ischaemia are disclosed in Published European Patent Application No. 346115.

Bisacetyl piperazines useful in the treatment of pain are described in U.S. Pat. Nos. 3,184,463, 3,324,128 and 3,347,860 and also Japanese Patent No. 67/2269 and International Patent Application No. 8801131.

Piperazine derivatives useful in the treatment or prevention of brain damage are described in U.S. Pat. No. 4,705,781 and European Patent Application No. 256890.

We have now found a novel group of piperazine derivatives which are selective kappa opioid receptor agonists. These compounds are therefore of interest in the treatment of conditions where the underlying aetiology indicates that treatment with a kappa opioid receptor agonist would be beneficial.

Thus, the present invention provides compounds of formula (I):

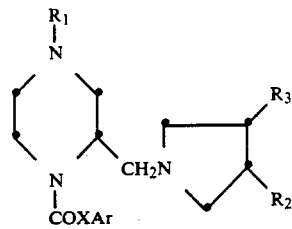

(I)

wherein
$R_1$ represents —$COR_4$, —$CO_2R_4$, —$COCO_2R_4$ or —$CONR_4R_5$ (where $R_4$ and $R_5$ may be the same or different and represent a hydrogen atom or a $C_{1-3}$alkyl group);
$R_2$ represents a hydrogen atom or a hydroxy or oxo group, with the proviso that when $R_1$ is —$COR_4$, —$CO_2R_4$ or —$COCO_2R_4$, $R_2$ is not a hydrogen atom;
$R_3$ represents a hydrogen atom or a hydroxy group;
X represents a direct bond, —$CH_2$— or —$CH_2O$—;
Ar represents a substituted phenyl moiety;
and physiologically acceptable salts thereof.

According to one embodiment the present invention provides compounds of formula (Ia):

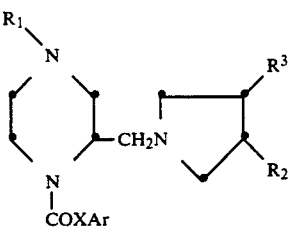

(Ia)

wherein
$R_1$ represents —$COR_4$, —$CO_2R_4$ or —$COCO_2R_4$ (where $R_4$ is a hydrogen atom or a $C_{1-3}$alkyl group);
$R_2$ represents a hydroxy or oxo group;
$R_3$ represents a hydrogen atom or a hydroxy group;
X represents a direct bond, —$CH_2$— or —$CH_2O$—;
Ar represents a substituted phenyl moiety;
and physiologically acceptable salts thereof.

According to another embodiment the present invention provides compounds of formula (Ib)

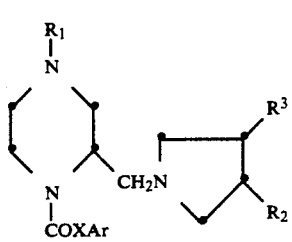

(Ib)

wherein
$R_1$ represents —$CONR_4R_5$ (where $R_4$ and $R_5$ are the same or different and are a hydrogen atom or a $C_{1-3}$alkyl group);
$R_2$ represents a hydrogen atom or a hydroxy or oxo group;
$R_3$ represents a hydrogen atom or a hydroxy group;
X represents a direct bond, —$CH_2$— or —$CH_2O$—;
Ar represents a substituted phenyl moiety;

and physiologically acceptable salts thereof.

As used herein, a $C_{1-3}$alkyl group may be straight or branched chain and is conveniently methyl, ethyl or propyl.

The term 'a substituted phenyl moiety' as used herein is a phenyl moiety substituted by one or more conventional substituents in the art. In the compounds of formula (I), Ar conveniently represents a phenyl moiety which is substituted by one or more electron-withdrawing substituents.

Suitable electron-withdrawing substituents include, for example, halogen (for example, fluorine, chlorine or bromine), $-CF_3$ or $-NO_2$. Ar is conveniently substituted at the meta and/or para positions on the phenyl ring by one or more halogens, for example chlorine and is typically a 3,4-dichlorophenyl moiety.

In one preferred class of compounds of formula (I), $R_1$ represents $-COR_4$.

In a further preferred class of compounds of formula (I), $R_1$ represents $-CO_2R_4$.

In another preferred class of compounds of formula (I), $R_1$ represents $-COCO_2R_4$.

$R_4$ conveniently represents a $C_{1-3}$alkyl group such as methyl, ethyl or propyl.

Conveniently $R_1$ may be, for example, a group $-COCH_3$ or a group $-CONHCH_3$.

In one preferred class of compounds of formula (I), $R_2$ represents a hydroxy group.

In another preferred class of compounds of formula (I), $R_3$ represents a hydrogen atom.

X preferably represents $-CH_2-$.

In a further preferred class of compounds of formula (I), Ar represents a halosubstituted phenyl moiety, in particular a chlorosubstituted phenyl moiety such as 3,4-dichlorophenyl.

Preferred compounds according to the invention include:

4-Acetyl-1-[(3,4-dichlorophenyl)acetyl]-2-[(3-hydroxy-1-pyrrolidinyl)methyl]piperazine;

4-Acetyl-1-[(3,4-dichlorophenyl)acetyl]-2-[(3-oxo-1-pyrrolidinyl)methyl]piperazine;

1-[(3,4-dichlorophenyl)acetyl]-2-[(3-hydroxy-1-pyrrolidinyl)methyl]-4-[(methylamino)carbonyl]piperazine;

and physiologically acceptable salts thereof.

A particularly preferred compound according to the invention is: [S*(R*S*)]4-acetyl-1-[(3,4-dichlorophenyl)acetyl]-2-[(3-hydroxy-1-pyrrolidinyl)methyl]piperazine, which has the following formula:

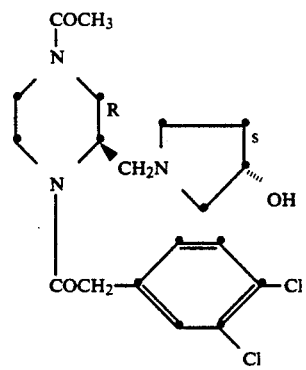

and its pharmaceutically acceptable salts.

Compounds of formula (I) contain at least one chiral centre and may exist in more than one stereoisomeric form. The invention includes within its scope all enantiomers, diastereomers and mixtures thereof.

It is believed that the activity of compounds falling within the scope of formula (I) resides primarily in the stereoisomeric form represented by formula (I')

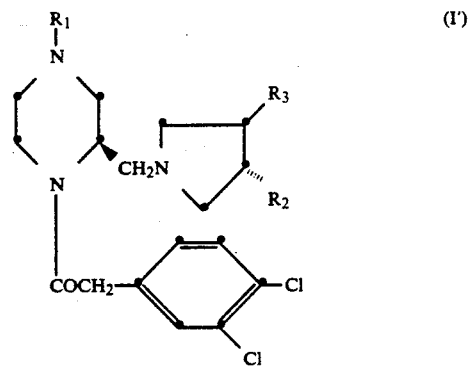

In a particularly preferred aspect the invention therefore provides compounds of formula (I) as described above having the stereoisomeric form represented by formula (I')

Suitable physiologically acceptable salts are those conventionally known in the art. Examples of physiologically acceptable salts include acid addition salts formed with inorganic acids, such as hydrochlorides, hydrobromides, phosphates and sulphates, and with organic acids, for example tartrates, maleates, fumarates, succinates and sulphonates. Other salts which are not pharmaceutically acceptable may be useful in the preparation of compounds of formula (I) and these form a further part of the invention.

Compounds of the invention may readily be isolated in association with solvent molecules by crystallisation from or evaporation of an appropriate solvent. It is intended to include such solvates within the scope of the present invention.

The kappa receptor activity of compounds falling within formula (I) has been demonstrated in vitro in the field stimulated rabbit vas deferens preparation using the procedure described by A. G. Hayes and A Kelly, *Eur. J. Pharmacol* 110, 317-322 (1985). It will be appreciated that kappa opioid receptor agonists may act at kappa receptors present in the central nervous system or in the periphery. Depending upon the condition to be treated it will be desirable to use a compound which is either centrally active or peripherally selective kappa receptor agonist. Certain compounds of the invention, in particular compounds of formula (Ic), have been found to be selective peripherally acting kappa receptor agonists. Selectivity of compounds of the invention for kappa receptors in the periphery has been demonstrated using the formalin test described by D. Dubuisson and S. G. Dennis, (1977), Pain 4, 161-174.

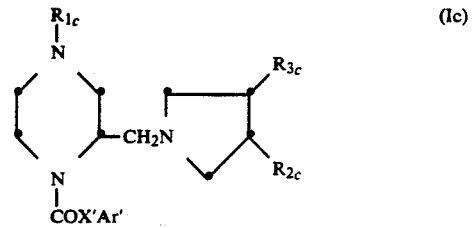

wherein
- $R_{1c}$ represents —$COR_{4c}$ or —$CONHR_{4c}$ (where $R_{4c}$ represents a hydrogen atom or a $C_{1-3}$alkyl group);
- $R_{2c}$ represents a hydroxy or oxo group;
- $R_{3c}$ represents a hydrogen atom or a hydroxy group;
- X' represents a direct bond, —$CH_2$— or —$CH_2O$;
- Ar' represents a substituted phenyl moiety; and physiologically acceptable salts thereof.

The invention also provides a compound of formula (I) or a physiologically acceptable salt thereof for use in medicine, in particular for the treatment of conditions where kappa agonists are indicated, in particular for the treatment of pain.

In an alternative or further aspect there is provided a method of treatment of a mammal, including man, comprising administration of an effective amount of a compound of formula (I) or a physiologically acceptable salt thereof in particular in the treatment of conditions where the use of a kappa receptor agonist is indicated, in particular for the treatment of pain.

The invention also provides the use of a compound of formula (I) or a physiologically acceptable salt thereof for the manufacture of a medicament for the treatment of conditions where kappa receptor agonists are indicated, for example, pain.

It will be appreciated that compounds of the invention are of use in the alleviation of established symptoms and in prophylaxis.

Compounds of the invention may be administered as the raw chemical but the active ingredient is preferably presented as a pharmaceutical formulation. The active ingredient may conveniently be presented in unit dose form.

According to another aspect, the invention provides a pharmaceutical composition comprising at least one compound of formula (I) or a physiologically acceptable salt thereof and formulated for administration by any convenient route conventional in the art. Such compositions are preferably in a form adapted for use in medicine, in particular human medicine and can conveniently be formulated in conventional manner using one or more pharmaceutically acceptable carriers or excipients. Compounds according to the invention may conveniently be formulated for oral, topical or parenteral administration.

For oral administration, the pharmaceutical compositions may take the form of, for example, tablets or capsules prepared by conventional means with pharmaceutically acceptable excipients such as binding agents (for example pregelatinised maize starch, polyvinylpyrrolidone or hydroxypropyl methylcellulose); fillers (for example lactose, microcrystalline cellulose or calcium phosphate); lubricants (for example magnesium stearate, talc or silica); disintegrants (for example potato starch or sodium starch glycollate); or wetting agents (for example sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (for example sorbitol syrup, methyl cellulose or hydrogenated edible fats); emulsifying agents (for example lecithin or acacia); non-aqueous vehicles (for example methyl or propyl-p-hydroxybenzoates or sorbic acid).

The compounds of the invention may be formulated for parenteral administration by injection conveniently intravenous or subcutaneous injection, for example by bolus injection or continuous intravenous infusion. Where the compounds are administered by continuous intravenous infusion this is conveniently sequential to a bolus injection. Formulations for injection may be presented in unit dosage form, for example, in ampoules or in multi-dose containers, with an added preservative.

The compounds may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, for example sterile pyrogen-free water, before use.

The compounds according to the invention may be formulated for topical administration in the form of ointments, creams, gels, lotions, shampoos, powders, (including spray powders), pessaries, tampons, sprays, dips, aerosols or drops (e.g. eye ear or nose drops). Ointments and creams may, for example, be formulated with an aqueous or oily base with the addition of suitable thickening and/or gelling agents.

Lotions may be formulated with an aqueous or oily base and will in general also contain one or more emulsifying agents, stabilising agents, dispersing agents, suspending agents, thickening agents, or colouring agents.

Powders may be formed with the aid of any suitable powder base. Spray powders will also contain a suitable propellant. Drops may be formulated with an aqueous or non aqueous base also comprising one or more dispersing agents, stabilising agents, solubilising agents or suspending agents. They may also contain a preservative.

Aerosol sprays are conveniently delivered from pressurised packs, with the use of a suitable propellant, e.g. dichlorodifluoromethane, trichlorofluoromethane, dichlorotetrafluoroethane, carbon dioxide or other suitable gas.

For topical administration by inhalation the compounds according to the invention may be delivered for use via a nebuliser.

It will be appreciated that the precise dose administered will depend on the age and condition of the patient, the particular compound used, and the frequency and route of administration. The compounds may be administered in single or divided doses and may be administered one or more times, for example 1 to 4 times, per day.

A proposed dose of the compounds of the invention is 0.001 to 100 mg/kg body weight, preferably 0.01 to 10 mg/kg body weight, most preferably 0.1 to 10 mg/kg body weight per day.

According to another aspect of the invention compounds of formula (I) and their physiologically acceptable salts may be prepared by the general method outlined below in which $R_1$, $R_2$, $R_3$, X and Ar are as defined for formula (I) unless otherwise indicated. It will be appreciated that in the method for preparing compounds of formula (I) given below it may be necessary or desirable to protect one or more sensitive groups in the molecule to prevent undesirable side reactions. Thus a reaction step comprising deprotection of a protected derivative of a compound of the invention may be required subsequent to the process described below. Protection and deprotection may be effected using conventional procedures as described, for example, in 'Protective Groups in Organic Synthesis', T. W. Greene (John Wiley & Sons, 1981).

According to one general process (A) compounds of formula (I) may be prepared by reacting a compound of formula (II)

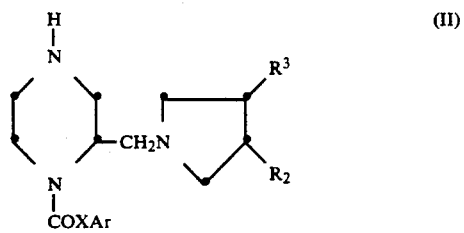

with a reagent serving to introduce the group —$R_1$.

Thus, for example, compounds of formula (I) may be prepared by reacting a compound of formula (II) with an acid $R_8CO_2H$ wherein $R_8$ represents $R_4$, $R_4O$— or $R_4O_2C$— as appropriate or an acylating agent corresponding thereto.

Suitable acylating agents corresponding to the acid $R_8CO_2H$ which may conveniently be used include, for example, acid halides (for example acid chlorides), alkyl esters (for example, methyl or ethyl esters) and mixed anhydrides. Such acylating agents may conveniently be prepared from the acid itself by conventional methods.

The reaction of a compound of formula (II) with an acid $R_8CO_2H$ is desirably effected in the presence of a coupling agent such as carbonyldiimidazole, dicyclohexylcarbodiimide or diphenylphosphoryl azide in a suitable reaction medium and conveniently at a temperature of from $-50°$ to $+50°$ C., preferably at ambient temperature. The reaction may be effected in a suitable reaction medium such as an ether (for example tetrahydrofuran), a haloalkane (for example, dichloromethane), a nitrile (for example acetonitrile), an amide (for example dimethylformamide), or mixtures thereof.

The reaction of a compound of formula (II) with an acylating agent corresponding to the acid $R_8CO_2H$ may conveniently be effected in a reaction medium and at a temperature as described above and optionally in the presence of a base. Suitable bases which may be employed include, for example, organic bases such as pyridine or triethylamine or inorganic bases such as calcium carbonate or sodium bicarbonate.

Compounds of formula (I) wherein $R_1$ is a group —$CONR_4H$ may be prepared by reacting a compound of formula (II) with an isocyanate $R_4N=C=O$ or a salt such as a sodium salt thereof.

The reaction of a compound of formula (II) with an isocyanate $R_4N=C=O$ or a salt thereof is desirably effected in a suitable reaction medium and conveniently at a temperature of from $-50°$ to $+100°$, preferably at ambient temperature. The reaction may be effected in a suitable reaction medium such as an ether (for example tetrahydrofuran), a haloalkane (for example dichloromethane), a nitrile (for example acetonitrile), an amide (for example dimethylformamide), water or mixtures thereof.

According to a further embodiment of process (A) compounds of formula (I) wherein $R_1$ is —$CONR_4R_5$ and $R_4$ and $R_5$ both represent $C_{1-3}$alkyl groups may be prepared by reacting a compound of formula (II) with a carbamoyl derivative $R_4R_5NCOY$ (where Y represents a readily displaceable atom or group). The reaction is conveniently carried out using a compound $R_4R_5NCOY$ wherein Y is a halogen atom such as chlorine or a group OR, where OR, is, for example, an acyloxy group such as an acetoxy group.

The reaction of a compound of formula (II) with a carbamoyl derivative $R_4R_5NCOY$ is desirably effected in a suitable reaction medium such as an ether (for example tetrahydrofuran), a nitrile (for example acetonitrile), a haloalkane (for example dichloromethane) and conveniently at a temperature of from $-50°$ to $+100°$, preferably at ambient temperature. The reaction may optionally be effected in the presence of a base. Suitable bases which may be employed include, for example, organic bases such as pyridine or triethylamine.

Compounds of formula (II) may conveniently be prepared from readily obtained starting materials by methods known in the art.

For example compounds of formula (II) may conveniently be prepared from compounds of formula (III)

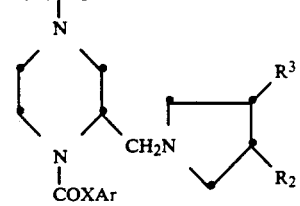

by removal of the benzyl group by conventional methods such as hydrogenation. Compounds of formula (III) may in turn be prepared by reductive amination of a compound of formula (IV)

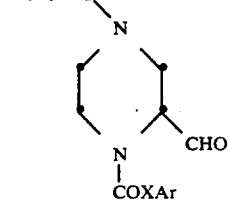

with an amine

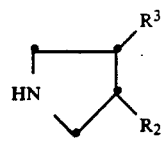

in the presence of a suitable reducing agent according to the method of process (C) below.

Compounds of formula (IV) may be prepared, for example, from compounds of formula (V)

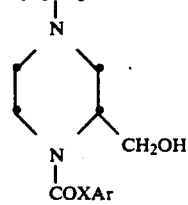

by oxidation using conventional methods, for example, using an oxidising agent such as an acid anhydride or acid chloride complex with dimethylsulphoxide (for example oxalylchloride-dimethylsulphoxide) in a solvent such as dichloromethane followed by treatment with a base such as triethylamine.

Compounds of formula (V) may themselves be prepared from compound (VI)

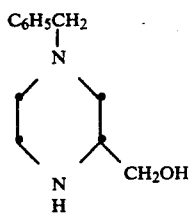
(VI)

by acylation to introduce the —COXAr moiety according to the method described above. The starting material compound (VI) is a known compound (see, for example European Patent Specification No. 68544).

The intermediates piperazines of formula (II) and (III) are novel compounds and form a further aspect of the invention.

According to another general process (B) compounds of formula (I) may be prepared by reacting a compound of formula (VII)

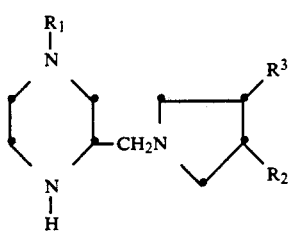
(VII)

with a reagent serving to introduce the group —COXAr.

For example a compound of formula (VII) may be reacted with an acid ArXCO$_2$H or an acylating agent corresponding thereto or a salt thereof.

Acylating agents corresponding to the acid ArXCO$_2$H which may be employed in process (B) include acid halides, for example acid chlorides, alkyl esters and mixed anhydrides as described previously for process (A).

The acylation reaction with an acid ArXCO$_2$H or an acylating agent corresponding thereto may be effected using similar reaction conditions to those described above for process (A).

Compounds of formula (VII) may be prepared from known compounds by conventional methods. For example, compounds of formula (VII) may be prepared from compounds of formula (VIII)

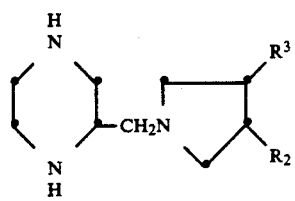
(VIII)

by a selective acylation at the piperazine 4-position using an appropriate acylating agent such as acetic anhydride in a polar solvent such as water. Compounds of formula (VIII) may in turn be prepared by hydrogenation of a compound of formula (IX) using conventional methods.

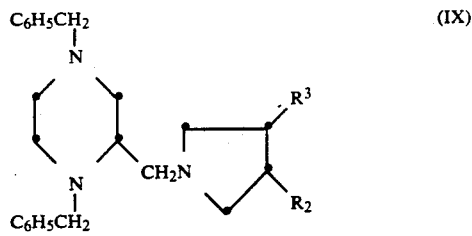
(IX)

Compounds of formula (IX) may be prepared, for example, from compound (X)

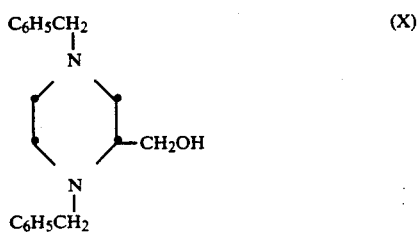
(X)

by oxidation followed by reductive amination according to the method of process (C) below. The oxidation is performed using conventional methods, for example using an oxidising agent such as an acid chloride complex with dimethylsulphoxide in a solvent such as dichloromethane followed by treatment with a base such as triethylamine.

According to a further general process (C), compounds of formula (I) may be prepared by reductive amination of a compound of formula (XI)

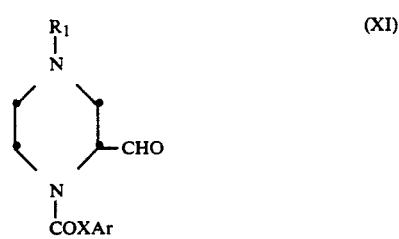
(XI)

with an amine

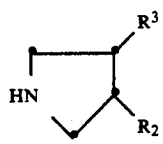

in the presence of a suitable reducing agent.

The reduction may be effected using an alkali metal or alkaline earth metal borohydride or cyanoborohydride (for example sodium borohydride or cyanoborohydride) in a suitable solvent, for example an alcohol such as methanol and at a suitable temperature, conveniently room temperature. The reaction may optionally be performed in the presence of an acid such as acetic acid.

Alternatively, the reduction may be effected catalytically, for example, using hydrogen in the presence of a metal catalyst such as Raney nickel, platinum, platinum oxide, palladium or rhodium which may be supported, for example, on charcoal. The reaction may conveniently be carried out in a suitable solvent such as an alcohol (for example ethanol), an amide (for example dimethylformamide) an ether (for example tetrahydrofuran) at a suitable temperature such as ambient temperature and optionally in the presence of an acid catalyst.

Compounds of formula (XI) may be prepared, for example, from compounds of formula (XII)

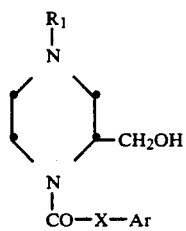

(XII)

by oxidation using conventional methods as described above.

Compounds of formula (XII) may themselves be prepared from the corresponding compound of formula (XIII)

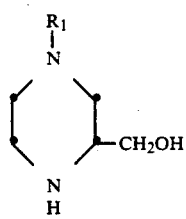

(XIII)

by methods analogous to those described for general process (B) above.

According to a further general process (D) a compound of formula (I) according to the invention may be converted into another compound of the invention using conventional procedures.

According to one embodiment of process (D) a compound of formula (I) containing an oxo group may be prepared by oxidation of the corresponding alcohol using a suitable oxidising agent, for example an acid anhydride or acid chloride complex with dimethylsulphoxide (such as oxalylchloride-dimethylsulphoxide) in a solvent such as dichloromethane, conveniently at low temperature, followed by treatment with a base such as triethylamine.

The general processes described above may yield the product of the general formula (I) as an individual stereoisomer or as a mixture of stereoisomers. Diastereoisomers may be separated at any convenient point in the overall synthesis by conventional methods for example chromatography. Specific enantiomers may be obtained by resolution of a racemic mixture at any convenient point in the overall synthesis by the use of conventional methods, see for example "Stereochemistry of Carbon Compounds by E. L. Eliel" (McGraw Hill, 1962).

Where it is desired to isolate a compound of the invention as a salt, this may be formed by conventional methods, for example by treatment with an acid or base in a suitable solvent such as an ether (for example diethyl ether), a nitrile (for example acetonitrile), a ketone (for example acetone) a halogenated hydrocarbon (for example dichloromethane) or an ester (for example ethyl acetate). Salts may also be formed by conversion of one salt into another using conventional methods.

Thus the product of any of process (A) to (D) above may be subjected to one or two further reactions comprising (i) converting a compound of formula (I) or a salt thereof into a physiologically acceptable salt thereof.

(ii) resolution of a racemic mixture to give a specific enantiomer.

The invention is further illustrated by the following non-limiting examples.

All temperatures are in °C. Chromatography was carried out in the conventional manner using silica gel (Merck, 7729) or by flash column chromatography on silica (Merck 9385) and thin layer chromatography (t.l.c) on silica except where otherwise stated. Dried refers to drying with $Na_2SO_4$ unless otherwise indicated.

EXAMPLE 1

4-Acetyl-1-[(3,4-dichlorophenyl)acetyl]-2-[(3-hydroxy-1-pyrrolidinyl) methyl]piperazine (i)

1-[(3,4-Dichlorophenyl)acetyl]-4-(phenylmethyl)-2-piperazinemethanol 1,1'-Carbonyldiimidazole (236 mg) was added to a stirred solution of 3,4-dichlorophenylacetic acid (314 mg) in dry dichloromethane (6 ml) at room temperature under nitrogen. The resulting solution was stirred at room temperature for 1 h and added dropwise to a cooled solution of 4-(phenylmethyl)-2-piperazinemethanol (300 mg) in dry dichloromethane (3 ml) and stirred at room temperature for 19 h. The reaction mixture was diluted with dichloromethane (5 ml) and washed with 2N sodium carbonate solution (3×10 ml). The organic layer was dried and evaporated to give an oil which was purified by flash column chromatography using gradient elution with dichloromethane:ethyl acetate (2:1), dichloromethane:ethyl acetate (1:1) and dichloromethane:methanol (9:1) to give the title compound as a solid (200 mg). m.p. 148°–150°.

(ii)

1-[(3,4-Dichlorophenyl)acetyl]-4-(phenylmethyl)-2-piperazine carboxaldehyde

A solution of dimethylsulphoxide (369 mg) in dry dichloromethane (3 ml) was added to a stirred solution of oxalyl chloride (300 mg) in dry dichloromethane (7 ml) at −60° under nitrogen and the resulting solution was stirred at −60° to −64° for 30 minutes. The product of stage (1) (774 mg) in dry dichloromethane (5 ml) was added dropwise and the reaction mixture was stirred between −60° to −63° for 2.5 h. Triethylamine (995 mg) was added and the mixture was allowed to warm to −20°, and quenched with water (15 ml). The layers were separated and the aqueous phase was further extracted with dichloromethane (2×15 ml). The combined organic extracts were dried and evaporated to give the title compound as an oil (830 mg).

T.l.c. ($SiO_2$) $CH_2Cl_2$:$CH_3OH$:0.880 $NH_3$ (150:8:1) Rf 0.8.

(iii)

1-[(3,4-Dichlorophenyl)acetyl]-4-(phenylmethyl)-2-[(3-hydroxy-1-pyrrolidinyl)methyl]piperazine A solution of the product of stage (ii) (3.67 g) in methanol (60 ml) was added to a stirred suspension of 3-pyrrolidinol (982 mg) and 3Å molecular sieves (3.68 g) in methanol (35 ml), followed by adjustment of the pH to 6 using methanolic hydrogen chloride solution. Sodium cyanoborohydride (1.30 g) was added portionwise and the resulting suspension was stirred under nitrogen for 19 h. The suspension was filtered and the filtrate evaporated to dryness. The residue was partitioned between aqueous 2N sodium carbonate solution (150 ml) and dichloromethane (100 ml) and the aqueous layer was further extracted with dichloromethane (2×50 ml)). The combined organic extracts were dried and evaporated to give an oil, which was purified by dry flash column chromatography on silica gel (Art. 7747): eluting with a mixture of dichloromethane:methanol:0.880 $NH_3$ (200:8:1) to give the title compound as a foam (2.38 g).

T.l.c. ($SiO_2$) $CH_2Cl_2$:$CH_3OH$:0.880 $NH_3$ (200:8:1). Rf. 0.12.

(iv)

1-[(3,4-Dichlorophenyl)acetyl]-2-[(3-hydroxy-1-pyrrolidinyl)methyl]piperazine dihydrochloride The product of stage (iii) (2.34 g) in a mixture of tetrahydrofuran (30 ml) water (30 ml) and concentrated hydrochloric acid (4.54 ml) was hydrogenated over 10% palladium oxide on carbon (50% paste) (1.93 g) at atmospheric pressure for 15 min. The catalyst was filtered off and washed thoroughly with a mixture of tetrahydrofuran and water. The filtrate was evaporated to dryness and the residue was triturated under dry diethyl ether. The resulting solid was dried in vacuo to give the title compound as a solid (1.99 g).

T.l.c. ($SiO_2$) $CH_2Cl_2$:$CH_3OH$:0.880 $NH_3$ (50:8:1) Rf 0.24.

(v)

4-Acetyl-1-[(3,4-dichlorophenyl)acetyl]-2-[(3-hydroxy-1-pyrrolidinyl)methyl]piperazine Acetyl chloride (187 mg) was added to a stirred solution of the product of stage (iv) (965 mg) and triethylamine (439 mg) in dry dichloromethane (25 ml) at 0° C. under nitrogen. The resulting solution was stirred at room temperature for 1.5 h. The reaction mixture was washed with aqueous 2N sodium carbonate solution (20 ml), the organic phase was dried and evaporated to give a foam. The residue was purified by flash column chromatography eluting with dichloromethane:methanol:0.880$NH_3$ (150:8:1) to give the title compound as a foam (730 mg).

Analysis: Found: C,53.76; H,6.19; N,9.69. $C_{19}H_{25}Cl_2N_3O_3$ 0.64 $H_2O$ requires C,53.59; H,6.22; N,9.87%.

EXAMPLE 2

4-Acetyl-1-[(3,4-dichlorophenyl)acetyl]-2-[(3-oxo-1-pyrrolidinyl)methyl]piperazine maleate A solution of dimethylsulphoxide (284 mg) in dry dichloromethane (3 ml) was added to a stirred solution of oxalyl chloride (231 mg) in dry dichloromethane (10 ml) at −55° C. under nitrogen. The resulting solution was stirred at −55°−−50° for 30 min, followed by dropwise addition of the compound of Example 1 (628 mg) in dry dichloromethane (5 ml) at −55° C. The reaction mixture was stirred at −60°-55° for 3 h. Triethylamine (398 mg) was added and the mixture was allowed to warm to −20° C., then quenched with water (10 ml). The layers were separated and the aqueous layer was further extracted with dichloromethane (2×10 ml). The combined organic extracts were dried and evaporated to give an oil which was purified by flash column chromatography eluting with dichloromethane:methanol:0.880 $NH_3$ (250:8:1) to give a foam (478 mg). A portion of the free base (151 mg) in ethyl acetate was treated with a solution of maleic acid (47 mg) in ethyl acetate. The resulting gum was triturated twice with dry diethyl ether to give the title compound as a solid (111 mg), m.p. softens 58°.

T.l.c. ($SiO_2$) $CH_2Cl_2$:$CH_3OH$:0.880 $NH_3$ (100:8:1). Rf. 0.54.

Analysis: Found: C,50.97; H,4.96; N,7.36. $C_{19}H_{23}Cl_2N_3O_3 \cdot C_4H_4O_4 \cdot 0.72$ $H_2O$ requires C,51.03; H,5.30; N,7.76%.

EXAMPLE 3

Methyl 4-[(3,4-dichlorophenyl)acetyl]-3-[(3-hydroxy-1-pyrrolidinyl) methyl]-1-piperazinecarboxylate A solution of methylchloroformate (243 mg) in dry dichloromethane (3 ml) was added dropwise to a stirred solution of 1-[(3,4-dichlorophenyl)acetyl]-2-[(3-hydroxy-1-pyrrolidinyl)methyl]piperazine dihydrochloride (1.0 g) and triethylamine (495 mg) in dry dichloromethane (25 ml) at −25° under nitrogen. The resulting solution was stirred at −30°−−25° for 30 min, quenched with aqueous 2N sodium carbonate solution (30 ml) and extracted with dichloromethane (3×20 ml). The combined organic extracts were dried and evaporated to give a foam. The residue was purified by flash column chromatography eluting with dichloromethane:methanol:0.880 $NH_3$ (150:8:1) to give the title compound as a foam (800 mg).

T.l.c. ($SiO_2$) $CH_2Cl_2$:$CH_3OH$:0.880 $NH_3$ (150:8:1) Rf 0.2.

Analysis: Found: C,51.50; H,5.98; N,9.22. $C_{19}H_{25}Cl_2N_3O_4 \cdot 0.6H_2O$ requires C,51.73; H,5.99; N,9.53%.

EXAMPLE 4

Methyl 4-[(3,4-dichlorophenyl)acetyl]-3-[(3-oxo-1-pyrrolidinyl) methyl]-1-piperazinecarboxylate maleate (1:1)

A solution of dimethylsulphoxide (301 mg) in dry dichloromethane (3 ml) was added to a stirred solution of oxalyl chloride (244 mg) in dry dichloromethane (10 ml) at −55° under nitrogen. The resulting solution was stirred at −55°−−50° for 30 min, followed by dropwise addition of the product of Example 3 (690 mg) in dry dichloromethane (5 ml) at −55°. The reaction mixture was stirred at −60°−−55° for 2.5 h. Triethylamine (632 mg) was added and the mixture was allowed to warm to −20°, and quenched with water (10 ml). The layers were separated and the aqueous layer was further extracted with dichloromethane (2×5 ml). The combined organic extracts were dried and evaporated to give an oil which was purified by flash column chromatography eluting with dichloromethane:methanol:0.880 $NH_3$ (250:8:1) to give the free base of the title compound (520 mg). A portion of the free base (116 mg) in ethyl acetate was treated with a solution of maleic acid (35 mg) in ethyl acetate. The resulting solid was washed with dry diethyl ether and crystallised from ethyl acetate/methanol to give the title compound as a solid (97 mg) m.p. 180°–183°.

T.l.c. (SiO$_2$) CH$_2$Cl$_2$:CH$_3$OH:0.880 NH$_3$ (100:8:1), Rf 0.56.

Analysis: Found: C,50.52; H,5.01; N,7.61. C$_{19}$H$_{23}$Cl$_2$N$_3$O$_4$.C$_4$H$_4$O$_4$ requires C,50.74; H,5.00; N,7.72%.

EXAMPLE 5

4-Acetyl-1-[4(Chlorophenyl)acetyl]-2-[(3-hydroxy-1-pyrrolidinyl)methyl]piperazine (i)
4-Acetyl-1-[(4-chlorophenyl)acetyl]-2-piperazinemethanol A mixture of 4-chlorophenylacetic acid (0.43 g) and 1,1'-carbonyldiimidazole (0.40 g) in dry dichloromethane (10 ml) was stirred at ambient temperature for 30 min. A solution of 4-acetyl-2-piperazinemethanol (0.16 g) in dry dichloromethane (5 ml) was added and the mixture was stirred at ambient temperature for 20 h. The reaction mixture was washed with aqueous sodium carbonate (1M; 25 ml), dried and evaporated in vacuo to give an oily residue (0.62 g). A solution of the residue in a mixture of tetrahydrofuran (5 ml) and water (5 ml) was treated with lithium hydroxide (63 mg) and the mixture was stirred at ambient temperature for 1 h. The organic solvent was removed in vacuo and the aqueous residue was extracted with dichloromethane (2×25 ml) filtered and evaporated in vacuo, to give an oily residue, which was purified by flash column chromatography eluting with dichloromethane:methanol:ammonia 200:8:1 to give the title compound as a white foam (0.23 g)

T.l.c. SiO$_2$/CH$_2$Cl$_2$/MeOH/NH$_3$ (150:8:1) Rf 0.15.

(ii)
4-Acetyl-1-[(4-chlorophenyl)acetyl]-2-[(3-hydroxy-1-pyrrolidinyl) methyl]piperazine A solution of oxalychloride (0.1 ml) in dry dichloromethane (3 ml) at −63° was treated with a solution of dimethylsulphoxide (0.21 ml) in dry dichloromethane (3 ml) over a 5 min period. The reaction mixture was treated with a solution of the product of stage (i) (0.21 g) in dry dichloromethane (3 ml) and the mixture was stirred at −70° for 2.5 h. Triethylamine (0.25 ml) was added at −70° and the reaction mixture was allowed to warm up to 0° when water (10 ml) was added. The mixture was diluted with dichloromethane (10 ml) and washed with aqueous sodium carbonate solution (1M; 5 ml). The organic solution was dried and evaporated to give an oily residue. A solution of the oil and pyrrolidinol (0.1 g) in methanol (5 ml) was acidified to pH6 with methanolic hydrogen chloride and 3 Å molecular sieves (0.1 g) and sodium cyanoborohydride (60 mg) were added. The mixture was stirred at ambient temperature for 20 h, and filtered through cotton wool. The filtrate was evaporated in vacuo and the residue was purified by flash column chromatography using dichloromethane:methanol:ammonia 200:10:2 as eluant to give the title compound as a white foam (80 mg).

Analysis: Found: C,58.00; H,6.89; N,10.55. C$_{19}$H$_{26}$ClN$_3$O$_3$.0.7H$_2$O requires C,58.14; H,7.04; N,10.71%.

EXAMPLE 6

[S(R*S*)]4-Acetyl-1-[(3,4-dichlorophenyl)acetyl]-2-[(3-hydroxy-1-pyrrolidinyl)methyl]piperazine (i) (S)-4-Acetyl-2-piperazinemethanol A solution of (S)-2-piperazinemethanol (1.25 g) in a mixture of water (12 ml) and triethylamine (3.2 ml) at ambient temperature was treated with a solution of acetic anhydride (1.25 ml; 1.32 mmol) in water (25 ml). The mixture was stirred at ambient temperature for 1 h, and anhydrous sodium carbonate (2 g) was added. The solvent was removed in vacuo. The residue was purified by flash column chromatography using dichloromethane:methanol:ammonia, 75:10:2 as eluant to give the title compound as a pale yellow oil (0.6 g).

T.l.c. SiO$_2$ Dichloromethane:methanol:ammonia (75:10:2) Rf 0.23.

(ii)
(S)-4-Acetyl-1-[(3,4-dichlorophenyl)acetyl]-2-piperazinemethanol

A solution of 1,1'-carbonyldiimidazole (3.2 g) and (3,4-dichlorophenyl) acetic acid (4.06 g) in dry dichloromethane (50 ml) was stirred at ambient temperature for 1 h. A solution of the product of stage (i) (0.6 g) in dry dichloromethane (10 ml) was added and the mixture was stirred for 18 h at ambient temperature. The reaction mixture was washed with aqueous sodium carbonate solution (2M; 50 ml) and the organic solution was evaporated in vacuo. The residue in tetrahydrofuran (30 ml) was treated with a solution of lithium hydroxide (0.8 g) in water (30 ml). The reaction mixture was stirred at ambient temperature for 1 h and the organic solvent was removed in vacuo. The residue was purified by flash column chromatography using dichloromethane:methanol:ammonia 80:10:1 as eluant to give the title compound as an off white foam (0.47 g).

T.l.c. SiO$_2$ Dichloromethane:methanol:ammonia (75:10:2) Rf 0.3.

(iii)
S-(-)-3-(Acetyloxy)-1-(phenylmethyl)-2,5-pyrrolidinedione

A mixture of acetyl chloride (20 ml) and L-malic acid (6.7 g) was heated under reflux for 2 h. The solvent was removed in vacuo, and the residue was diluted with dichloromethane (100 ml). Benzylamine (20 ml) was added and the mixture was stirred at ambient temperature for 20 h. Acetyl chloride (20 ml) was added, and the mixture was heated under reflux for 5 h. The solvent was removed in vacuo and the solid residue was purified by dry flash column chromatography using ethyl acetate: hexane 1:3 as eluant to give the title compound as a solid (11.5 g)

M.p. 58°–60°. [α]$_D^{20}$-40.61 [1.0%, w/v MeOH]

(iv) S-(-)-1-(Phenylmethyl)-3-pyrrolidinol

To a suspension of lithium aluminium hydride (2.45 g) in dry tetrahydrofuran (50 ml), was added a solution of the product of stage (iii) (5.05 g) in dry tetrahydrofuran (50 ml) so as to maintain a gentle reflux. The mixture was stirred at ambient temperature for 3 h and heated at reflux for 1 h. The cooled reaction mixture was cautiously treated with water (2.4 ml) followed by aqueous sodium hydroxide (2M; 7.5 ml) and water (2.5 ml). The mixture was filtered through hyflo and the filtrate was evaporated in vacuo to give an oily residue (4.5 g). This was purified by flash column chromatography with dichloromethane:methanol:ammonia (150:8:1) as eluant to give the title compound as a colourless oil (2.8 g).

T.l.c. SiO$_2$ (CH$_2$Cl$_2$:MeOH:NH$_3$; 150:8:1). Rf. 0.25. [α]$_D^{20}$ -1.02° (0.7%; w/v MeOH).

(v) S-(-)-3-Pyrrolidinol

A solution of the product of stage (iv) (2.65 g) in a mixture of ethanol (30 ml) and acetic acid (1 ml) was hydrogenated over 10% palladium on carbon (10%; 50% wet 1 g). The solvent was removed in vacuo and the residue was dissolved in a solution of potassium hydroxide (1 g) in ethanol (20 ml). The solvent was removed in vacuo, and the residue was extracted with dichloromethane (2×50 ml). The organic extract was filtered and evaporated. The residue was purified by distillation under reduced pressure, to give the title compound as a colourless oil (1.11 g).

T.l.c. SiO$_2$ CH$_2$Cl$_2$:MeOH:NH$_3$; (75:10:2) Rf. 0.05. [α]$_D$ -5.18° [MeOH; 1.0% w/v].

(vi) [S*(R*S*)]
4-Acetyl-1-[3,4-dichlorophenyl)acetyl]-2-[(3-hydroxy-1-pyrrolidinyl)methyl]piperazine A solution of oxalylchloride (0.2 ml) in dry dichloromethane (6 ml) at -70° was treated with a solution of dry dimethylsulphoxide (0.3 1ml) in dry dichloromethane (5 ml) over a 5 min period. The mixture was stirred at -70° for 0.5 h and a solution of the product of stage (ii) (0.45 g) in dry dichloromethane (5 ml) was added. Stirring was continued at -70° for 2.5 h and a solution of N-methylmorpholine (0.5 ml) in dry dichloromethane (2 ml) was added. The mixture was stirred at -20° to -15° for 25 min, and then poured into ice-cold hydrochloric acid (0.02M; 75 ml). The product was extracted with dichloromethane (2×50 ml). The combined organic extracts were dried and evaporated to give an oily residue.

A solution of the product of stage (v) (0.5 g) in methanol (5 ml) was treated with ethereal hydrogen chloride (pH 6.5), and cooled to -20°. A solution of the aldehyde in methanol (5 ml) was added, followed by 3 Å Molecular sieves (0.2 g) and sodium cyanoborohydride (0.2 g).

The mixture was stirred at ambient temperature for 18 h, filtered and evaporated in vacuo. The residue was dissolved in dichloromethane (50 ml) and washed with aqueous sodium carbonate solution. The organic solution was dried and evaporated in vacuo to give an oily residue which was purified by flash column chromatography using dichloromethane:methanol:ammonia, 150:8:1 as eluent to give a white foam (0.28 g).

The solid was crystallized from methyl acetate/hexane to give the title compound as a white solid (0.15 g) m.p. 133°.

Analysis: Found: C,54.82; H,5.97; N,9.84. C$_{19}$H$_{25}$Cl$_2$N$_3$O$_3$ requires C,55.08; H,6.08; N,10.14%.

EXAMPLE 7

[S(R*S*)] and [S(R*R*)]
4-Acetyl-1-1-[(3,4-dichlorophenyl)acetyl]-2-[(3-hydroxy-1-pyrrolidinyl)methyl]piperazine A solution of oxalylchloride (0.2 ml) in dry dichloromethane (6 ml) at -70° was treated with a solution of dry dimethylsulphoxide (0.31 ml) in dry dichloromethane (3 ml) over a 5 min period. The mixture was stirred at -70° for 30 min, and a solution of the product of Example 5, stage (i) (0.52 g) in dry dichloromethane (5 ml) was added. The mixture was stirred at -70° for 2.5 h, triethylamine (2.5 ml) was added, and the mixture was allowed to warm to -20° when water (5 ml) was added. The product was extracted with dichloromethane (20 ml) and the organic extract was washed with aqueous sodium carbonate solution (2×15 ml), dried and evaporated to give an oily residue. A solution of the residue and S-pyrrolidinol (0.25 g) in methanol (10 ml) was treated with methanolic hydrogen chloride until pH was 6-6.5. 3 Å molecular sieves (0.2 g) and sodium cyanoborohydride (0.2 g) were added and the mixture was stirred at ambient temperature for 18 h.

The reaction mixture was filtered and the filtrate was evaporated in vacuo. The residue was dissolved in dichloromethane (50 ml) and was washed with aqueous sodium carbonate solution (1M; 20 ml). The organic solution was dried and evaporated to give a gum, which was purified by flash column chromatography using dichloromethane:methanol:ammonia 150:8:1 as eluant to give an oil.

The oil was further purified by HPLC Spherisorb SPW5 column using hexane:ethanol:ammonia 1300:700:15 as eluant to give two fractions. The early eluting fraction was crystallised from methyl acetate/hexane to give the title compound (isomer 1) (0.04 g) m.p. 131°-133°.

Analysis: Found: C,54.85; H,6.00; N,9.81. C$_{19}$H$_{25}$Cl$_2$N$_3$O$_3$ requires C,55.08; H,6.08; N,10.14%.

The later eluting fraction was evaporated in vacuo to give the title compound (isomer 2) as a white foam (0.1 g).

Analysis Found: C,54.52; H,6.31; N,9.41. C$_{19}$H$_{25}$Cl$_2$N$_3$O$_3$.0.15H$_2$O requires: C,54.72; H,6.12; N,10.08%

EXAMPLE 8

1-[(3,4-Dichlorophenyl)acetyl]-2-[(3-hydroxy-1-pyrrolidinyl)methyl]-4-[(methylamino)carbonyl]piperazine (i)
1-[(3,4-Dichlorophenyl)acetyl]-4-(phenylmethyl)-2-piperazinemethanol 1,1'-Carbonyldiimidazole (236 mg) was added to a stirred solution of 3,4-dichlorophenylacetic acid (314 mg) in dry dichloromethane (6 ml) at room temperature under nitrogen. The resulting solution was stirred at room temperature for 1 h and added dropwise to a cooled solution of 4-(phenylmethyl)-2-piperazinemethanol (300 mg) in dry dichloromethane (3 ml) and stirred at room temperature for 19 h. The reaction mixture was diluted with dichloromethane (5 ml) and washed with 2N sodium carbonate solution (3×10 ml). The organic layer was dried and evaporated to give an oil which was purified by flash column chromatography using gradient elution from dichloromethane:ethyl acetate (2:1) to dichloromethane:ethyl acetate (1:1) to dichloromethane:methanol (9:1) to give the title compound as a solid (200 mg). m.p. 148°-150°.

(ii)
1-[(3,4-Dichlorophenyl)acetyl]-4-(phenylmethyl)-2-piperazine carboxaldehyde A solution of dimethylsulphoxide (369 mg) in dry dichloromethane (3 ml) was added to a stirred solution of oxalyl chloride (300 mg) in dry dichloromethane (7 ml) at -60° under nitrogen and the resulting solution was stirred at -60° to -64° for 30 minutes. The product of stage (i) (774 mg) in dry dichloromethane (5 ml) was added dropwise and the reaction mixture was stirred between −60° to −63° for 2.5 h. Triethylamine (995 mg) was added and the mixture was allowed to warm to −20°, and quenched with water (15 ml). The layers were separated and the aqueous phase was further extracted with dichloromethane (2×15 ml). The combined organic extracts were dried and evaporated to give the title compound as an oil (830 mg).

(iii)
1-[(3,4-Dichlorophenyl)acetyl]-4-(phenylmethyl)-2-[(3-hydroxy-1-pyrrolidinyl)methyl]piperazine A solution of the product of stage (ii) (3.67 g) in methanol (60 ml) was added to a stirred suspension of 3-pyrrolidinol (982 mg) and 3 Å molecular sieves (3.68 g) in methanol (35 ml), followed by adjustment of the pH to 6 using methanolic hydrogen chloride solution. Sodium-cyanoborohydride (1.30 g) was added portionwise and the resulting suspension was stirred under nitrogen for 19 h. The suspension was filtered and the filtrate evaporated to dryness. The residue was partitioned between aqueous 2N sodium carbonate solution (150 ml) and dichloromethane (100 ml) and the aqueous layer was further extracted with dichloromethane (2×50 ml)). The combined organic extracts were dried and evaporated to give an oil, which was purified by dry flash column chromatography on silica gel eluting with a mixture of dichloromethane:methanol:0.880 NH$_3$ (200:8:1) to give the title compound as a foam (2.38 g).

T.l.c. (SiO$_2$) CH$_2$Cl$_2$:CH$_3$OH:0.880 NH$_3$ (200:8:1). Rf. 0.12.

(iv)
1-[(3,4-Dichlorophenyl)acetyl]-2-[(3-hydroxy-1-pyrrolidinyl)methyl]piperazine dihydrochloride The product of stage (iii) (2.34 g) in a mixture of tetrahydrofuran (30 ml) water (30 ml) and concentrated hydrochloric acid (4.54 ml) was hydrogenated over 10% palladium oxide on carbon (50% paste) (1.93 g) at atmospheric pressure for 15 min (268 ml). The catalyst was filtered off and washed thoroughly with a mixture of tetrahydrofuran and water. The filtrate was evaporated to dryness and the residue was triturated under dry diethyl ether. The resulting solid was dried in vacuo to give the title compound as a solid (1.99 g).

T.l.c. (SiO$_2$) CH$_2$Cl$_2$:CH$_3$OH: 0.880 NH$_3$ (50:8:1) Rf 0.24.

(v)
1-[(3,4-Dichlorophenyl)acetyl]-2-[(3-hydroxy-1-pyrrolidinyl) methyl]-4-[(methylamino)carbonyl]piperazine A mixture of the product of stage (iv) (0.25 g) and triethylamine (0.16 ml) in dry acetonitrile (5 ml) was treated with a solution of methyl isocyanate (0.062 g) in dry acetonitrile (1 ml). The mixture was stirred at ambient temperature for 1 hour and the solvent was removed in vacuo. The residue was purified by flash column chromatography eluting with dichloromethane methanol/ammonia 200:8:1 to give the title compound as a foam (0.18 g) m.p. 57° softens.

Assay: Found: C,54.07; H,7.26; N,12.86. C$_{19}$H$_{26}$Cl$_2$N$_4$O$_3$.0.4C$_6$H$_{15}$N.0.5H$_2$O  C,53.68; H,6.95; N,12.87%.

EXAMPLE 9

1-[(3,4-Dichlorophenyl)acetyl]-4-[(methylamino)carbonyl]-2-(1-pyrrolidinylmethyl)piperazine (i)
1-[(3,4-Dichlorophenyl)acetyl]-4-(phenylmethyl)-2-(1-pyrrolidinylmethyl)piperazine maleate A solution of the product of Example 8 stage (ii) (825 mg) in methanol (10 ml) was added to a stirred suspension of pyrrolidine (180 mg) and 3 Å molecular sieves (800 mg) in methanol (5 ml), the pH of the mixture being adjusted to 6.5–7 using methanolic hydrogen chloride solution. The reaction mixture was stirred under nitrogen for 15 min and sodium cyanoborohydride (269 mg) was added portionwise. The resulting suspension was stirred under nitrogen for 17 h, filtered and the filtrate was evaporated to dryness. The residue was partitioned between 2N sodium carbonate (30 ml) and dichloromethane (30 ml) and the aqueous layer was further extracted with dichloromethane (2×15 ml). The combined organic extracts were dried and evaporated to give a gum which was purified by flash column chromatography eluting with dichloromethane:methanol:0.880 aqueous ammonia (250:8:1) followed by re-purification on an alumina column (UGII, diameter 2.5 cm); eluting with mixtures of ether:methanol (99:1/98:2) to give the free base of the title compound as an oil (181 mg)

A portion of the free base (84 mg) in ethyl acetate was treated with a solution of maleic acid (24 mg) in ethyl acetate to give the title compound as a solid (72 mg) m.p. 117°–120°.

(ii)
1-[(3,4-Dichlorophenyl)acetyl]-2-(1-pyrrolidinylmethyl)piperazine maleate (1:1)

The free base of the product of stage (i) (697 mg) in a mixture of tetrahydrofuran: water (1:1) (14 ml) and concentrated hydrochloric acid (1.4 ml) was hydrogenated over 10% palladium on carbon (50% paste) (560 mg) at atmospheric pressure. The catalyst was filtered off, the filtrate was evaporated and the residue was diluted with water (15 ml) and basified with 2N sodium carbonate solution. The aqueous layer was extracted with dichloromethane (3×15 ml) and the combined organic extracts were dried and evaporated to give an oil (526 mg). Purification by flash column chromatography eluting with dichloromethane methanol:0.880 aqueous ammonia (100:8:1) gave the free base of the title compound as an oil (479 mg), a portion of which (60 mg) in ethyl acetate (2 ml) was treated with a solution of maleic acid (39 mg) in ethyl acetate (2 ml). The resulting solid was crystallised from ethyl acetate/methanol to give the title compound as a solid (35 mg) m.p. 160°–162°.

(iii)
1-[(3,4-Dichlorophenyl)acetyl]-4-[(methylamino)carbonyl]-2-(1-pyrrolidinylmethyl)piperazine Methyl isocyanate (61 mg) was added to a stirred solution of the free base of the product of stage (ii) (200 mg) in dry acetonitrile (3 ml) under nitrogen. The resulting mixture was stirred at room temperature for 1 h. The solvent was removed in vacuo to give a foam (216 mg), which was purified by flash column chromatography on silica gel eluting with dichloromethane:methanol:0.880 NH₃ (150:8:1) to give the title compound as a foam (104 mg) softens 45°–48°.

Analysis: Found: C,54.12; H,6.20; N,13.03. $C_{19}H_{26}Cl_2N_4O_2 \cdot 0.5H_2O$ requires C,54.03; H,6.44; N,13.26%.

EXAMPLE 10

4-[(3,4-Dichlorophenyl)acetyl]-3-(1-pyrrolidinylmethyl)-1-piperazinecarboxamide A solution of 1-[(3,4-dichlorophenyl)acetyl]-2-(1-pyrrolidinylmethyl) piperazine (200 mg) in acetic acid (0.5 ml) and water (1 ml) was treated with a solution of sodium cyanate (73 mg) in water (0.5 ml). The resulting solution was stirred at room temperature for 2 h. The solvent was removed in vacuo, the residue was basified with aqueous 2N sodium carbonate solution and extracted with dichloromethane (2×25 ml). The combined organic extracts were dried and evaporated to give a foam (206 mg) which was purified by flash column chromatography eluting with dichloromethane:methanol:0.880 NH₃ (200:8:1) to give a solid (120 mg). Crystallisation from ethyl acetate/methanol gave the title compound as a solid (58 mg) m.p. 206°–209° C.

Analysis Found: C,54.13; H,6.10; N,13.80. $C_{18}H_{24}Cl_2N_4O_2$ requires C,54.14; H,6.06; N,14.03%.

EXAMPLE 11

4-[(3,4-Dichlorophenyl)acetyl]-N,N-dimethyl-3-(1-pyrrolidinylmethyl)-1-piperazinecarboxamide Dimethylcarbamyl chloride (66 mg) was added to a stirred solution of 1-[(3,4-dichlorophenyl)acetyl]-2-(1-pyrrolidinylmethyl)piperazine (200 mg), pyridine (53 mg) and 4-dimethylaminopyridine (5 mg) in dry dichloromethane at 0° for 4.5 h. The reaction mixture was washed with aqueous 2N sodium carbonate solution (2×10 ml), dried and evaporated to give an oil, which was purified by flash column chromatography eluting with dichloromethane:methanol:0.880 NH₃ (200:8:1) to give the title compound as an oil (195 mg).

Analysis Found: C,54.41; H,6.50; N,12.64; $C_{20}H_{28}Cl_2N_4O_2 \cdot 0.25\ CH_2Cl_2$ requires C,54.22; H,6.40; N,12.49%

T.l.c. (SiO₂) CH₂Cl₂:CH₃OH:0.880 NH₃ (100:8:1) Rf 0.51.

TABLETS FOR ORAL ADMINISTRATION

| DIRECT COMPRESSION | mg/tablet |
| --- | --- |
| Active ingredient | 20 |
| Calcium Hydrogen Phosphate B.P.* | 75.5 |
| Croscarmellose sodium USP | 4 |
| Magnesium Stearate B.P. | 0.5 |
| Compression weight | 100 mg |

*of a grade suitable for direct compression

The active ingredient is sieved before use. The calcium hydrogen phosphate, croscarmellose sodium and active ingredient are weighed into a clean polythene bag. The powders are mixed by vigorous shaking then the magnesium stearate is weighed and added to the mix which is blended further. The mix is then compressed using a Manesty F3 tablet machine fitted with 5.5 mm flat bevelled edge punches, into tablets with target compression weight of 100 mg.

Tablets may also be prepared by other conventional methods such as wet granulation.

Tablets of other strengths may be prepared by altering the ratio of active ingredient to lactose or the compression weight and using punches to suit.

The tablets may be film coated with suitable film forming materials, such as hydroxypropyl methylcellulose, using standard techniques. Alternatively the tablets may be sugar coated.

| | mg/ml |
| --- | --- |
| INJECTION FOR INTRAVENOUS ADMINISTRATION | |
| Active ingredient | 5 |
| Sodium Chloride BP | as required |
| Water for Injection BP 0.5 to 2 ml | |
| INTRAVENOUS INFUSION | |
| Dextrose 5 aqueous solution BP | 10–100 ml |
| Aotive ingredient | 700 mg |
| Sodium Chloride BP | as required |

For infusion at a rate of 700 mg per hour.

Sodium chloride may be added to adjust the tonicity of the solution and the pH may be adjusted, using acid or alkali, to that of optimum stability and/or to facilitate solution of the active ingredient. Alternatively suitable buffer salts may be used.

The solution is prepared, clarified and filled into appropriate size ampoules sealed by fusion of the glass. The injection is sterilised by heating in an autoclave using one of the acceptable cycles. Alternatively the solution may be sterilised by filtration and filled into sterile ampoules under aseptic conditions. The solution may be packed under an inert atmosphere of nitrogen or other suitable gas.

We claim
1. A compound of formula (I)

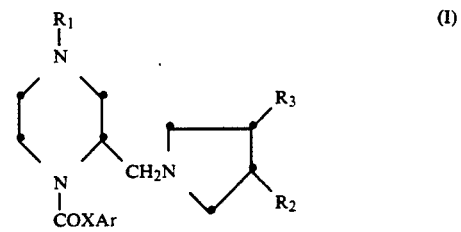

wherein
R₁ represents —COR₄, —COCO₂R₄ or —CONR₄R₅ (where R₄ and R₅ may be the same or different and represent a hydrogen atom or a C₁₋₃alkyl group);
R₂ represents a hydrogen atom or a hydroxy or oxo group, with the proviso that when R₁ is —COR₄, or —COCO₂R₄, R₂ is not a hydrogen atom;
R₃ represents a hydrogen atom or a hydroxy group;
X represents a direct bond, —CH₂— or —CH₂O—;
Ar represents a substituted phenyl moiety;
or a physiologically acceptable salt thereof.

2. A compound according to claim 1 wherein R₁ represents —COR₄.

3. A compound according to claim 1 wherein R₁ represents —CONR₄R₅.

4. A compound according to claim 1 wherein R₁ represents —COR₄ or —CONR₄H; R₂ represents a hydroxy or oxo group; and R₃ represents a hydrogen atom or a hydroxy group.

5. A compound according to claim 1 wherein R₂ represents a hydroxy group.

6. A compound according to claim 1 wherein $R_3$ represents a hydrogen atom.

7. A compound according to claim 1 wherein X represents —$CH_2$—.

8. A compound according to claim 1 wherein Ar represents halosubstituted phenyl.

9. A pharmaceutical composition which comprises an analgesically effective amount of a compound of formula (I) as defined in claim 1 or a physiologically acceptable salt thereof together with a pharmaceutically acceptable carrier therefor.

10. A method of treating a human suffering from pain which comprises administering an effective amount of a compound of formula (1c)

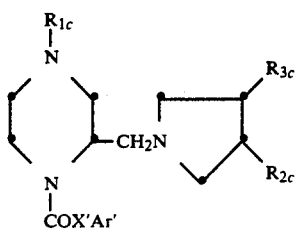
(Ic)

wherein $R_{1c}$ represents —$COR_{4c}$ or —$CONHR_{4c}$, wherein $R_{4c}$ represents a hydrogen atom or a $C_{1-3}$alkyl group;

$R_{2c}$ represents a hydroxy or oxo group;

$R_{3c}$ represents a hydrogen atom or a hydroxy group;

X' represents a direct bond, —$CH_2$— or —$CH_2O$;

Ar' represents a substituted phenyl moiety;

or a physiologically acceptable salt thereof.

11. A compound according to claim 1 wherein $R_1$ represents —$COCO_2R_4$.

12. A compound of formula (1c)

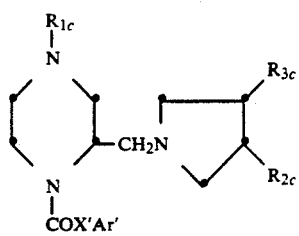
(Ic)

wherein $R_{1c}$ represents —$COR_{4c}$ or —$CONHR_{4c}$, wherein $R_{4c}$ represents a hydrogen atom or a $C_{1-3}$alkyl group;

$R_{2c}$ represents a hydroxy or oxo group;

$R_{3c}$ represents a hydrogen atom or a hydroxy group;

X' represents a direct bond, —$CH_2$— or —$CH_2O$;

Ar' represents a substituted phenyl moiety;

or a physiologically acceptable salt thereof.

13. A compound according to claim 12 which is a selective peripherally acting kappa receptor agonist.

14. A compound according to claim 2 wherein $R_2$ represents a hydroxy group.

15. A compound according to claim 3 wherein $R_2$ represents a hydrogen group.

16. A compound according to claim 2 wherein $R_3$ represents a hydrogen atom.

17. A compound according to claim 3 wherein $R_3$ represents a hydrogen atom.

18. A compound according to claim 5 wherein $R_3$ represents a hydrogen atom.

19. A compound according to claim 4 wherein X represents —$CH_2$.

20. A compound according to claim 4 wherein Ar represents halosubstituted phenyl.

* * * * *